United States Patent [19]

Pineau et al.

[11] Patent Number: 5,780,424
[45] Date of Patent: Jul. 14, 1998

[54] PURIFIED RIBOSOMAL FRACTIONS SEPARATED FROM THE NONPHOTOSYNTHETIC FILAMENTOUS BACTERIA BEGGIATOALES

[75] Inventors: Nathalie Pineau, Poitiers; Lionel Breton, Versailles; Richard Martin, Rochecorbon, all of France

[73] Assignee: Société L'Oréal S.A., Paris, France

[21] Appl. No.: 723,760

[22] Filed: Sep. 30, 1996

[30] Foreign Application Priority Data

Sep. 28, 1995 [FR] France ................................ 95 11404

[51] Int. Cl.$^6$ .................. A61K 38/00; A61K 31/70; A61K 39/02; A61K 9/14
[52] U.S. Cl. ................. 514/2; 514/44; 514/885; 514/886; 514/887; 424/489; 424/490; 424/234.1; 424/282.1; 435/820
[58] Field of Search .................. 514/42, 44, 2, 514/885, 886, 887; 424/489, 490, 234.1, 282.1; 435/820

[56] References Cited

FOREIGN PATENT DOCUMENTS

| 0238407 | 9/1987 | European Pat. Off. . |
| 0657530 | 6/1995 | European Pat. Off. . |
| 2693654 | 1/1994 | France . |
| 2700172 | 7/1994 | France . |

OTHER PUBLICATIONS

K. P. Schaal, The Genera Actinomyces, Arcanobacterium, and Rothia, in The Prokaryotes, A Handbook on the Biology of Bacteria: Ecophysiology, Isolation, Identification, Applications, vol. 1, 2nd Ed., Chapter 38, pp. 850–868, 1992.

Cancer Research, vol. 40, May 1980, pp. 1501–1505, Urban et al: "Tumor–Immunotherapeutic Efficacy of Serratia Marcescens Polyribosomes".

*Primary Examiner*—David M. Naff
*Assistant Examiner*—Janet M. Kerr
*Attorney, Agent, or Firm*—Burns, Doane, Swecker & Mathis, L.L.P.

[57] ABSTRACT

Variously pure ribosomal fractions separated from at least one nonphotosynthetic filamentous bacterium are well suited for formulation into a variety of cosmetic/pharmaceutical compositions, for example for the immunostimulation of the immune system of the skin.

11 Claims, No Drawings

PURIFIED RIBOSOMAL FRACTIONS SEPARATED FROM THE NONPHOTOSYNTHETIC FILAMENTOUS BACTERIA BEGGIATOALES

BACKGROUND OF THE INVENTION

1. Technical Field of the Invention

The present invention relates to variously pure ribosomal fractions separated from at least one nonphotosynthetic filamentous bacterium.

2. Description of the Prior Art

Ribosomes are corpuscular formations having a size of 140 to 230 angstroms, consisting of ribonucleic acids which are associated with proteins and which are present in the cells of all organisms, in particular bacteria. Ribosomes are the site of the complex reactions which permit the synthesis of proteins by virtue of the multienzymatic complex of which they are constituted.

In prokaryotes the ribosomes have a sedimentation constant of the order of 70 S (svedberg: an international unit measuring the rate of sedimentation of bodies subjected to a standard centrifuging).

Morphologically, ribosomes are divided into 2 subunits of unequal sizes by a cleft which is perpendicular to their large axis. These 2 subunits have a sedimentation constant on the order of 50 S and 30 S, respectively. The 50 S subunit contains two ribonucleic acids of 23 S and 5 S, respectively, and about thirty proteins, whereas the 30 S subunit contains a 16 S ribonucleic acid and about twenty proteins.

It will therefore be appreciated that the expression "ribosomal fraction" corresponds to the ribosome-enriched fraction of a medium which can be obtained, for example after centrifuging, by separating the various organites constituting the cells of an organism.

Thus, whatever its degree of purity may be, a ribosomal fraction may therefore contain either at least one entire ribosome, or at least one constituent element of a ribosome or a constituent element of one of the subunits of a ribosome.

At present ribosomal fractions are employed, for example, in cosmetics in the preparation of compositions intended to delay or retard skin aging by stimulation of cell growth and modulation of the maturing of the connective tissue (EP-A-631,773). In medicine there are known compositions which are intended to reinforce the immunity defenses, in particular of patients who have suffered severe burns and who are as a result sensitive to opportunist infections caused by bacteria, viruses or fungi (WO 91/11,174) or else with regard to the diseases of the otorhinolaryngological region (FR-2,253,499, FR-2,360,314, FR-2,388,563, FR-2,674,755 and ZA-8,801,071), and allergies (U.S. Pat. No. 4,946,945). Ribosomal fractions are also employed in the preparation of adjuvants for vaccines (FR-2,374,911 and DE-1,617,809). In general, the ribosomal fractions employed in this prior art are prepared from gram-negative bacteria, such as for example, those of the Enterobacteriaceae family (e.g., *Klebsiella pneumoniae, Escherichia coli, Serratia marcessens*), or from the Pasteurellaceae family (e.g., *Haemophilus influenzae*), or from gram-positive bacteria, such as, for example, those of the Bacillus family (e.g., *Bacillus subtilis*), of the Streptococcaceae family (e.g., *Streptococcus pneumoniae, Streptococcus pyogenes* Gr. A), or of the Lactobacillaceae family (e.g., Acidophilus, Bifidum), or from yeasts, such as, for example, *Candida albicans* or *Candida tropicalis*.

Although the ribosomal fractions of the prior art are satisfactory, need continues to exist to identify and investigate novel ribosomal fractions separated from organisms which to date have not been employed in this field.

SUMMARY OF THE INVENTION

Accordingly, a major object of the present invention is the provision of novel ribosomal fractions suitable for use in the technical fields indicated above, and potentially also in yet other fields of scientific endeavor.

Briefly, the present invention features novel ribosomal fractions prepared and separated from at least one nonphotosynthetic filamentous bacterium.

DETAILED DESCRIPTION OF BEST MODE AND SPECIFIC/PREFERRED EMBODIMENTS OF THE INVENTION

More particularly according to the present invention, as indicated above, whatever its degree of purity, the ribosomal fraction may contain either at least one entire ribosome, or at least one constituent element of a ribosome, or a constituent element of one of the subunits of a ribosome.

The immune system includes a set of specialized cells which are subject to many control mechanisms ensuring their renewal, their activation and their differentiation, which are indispensable to a normal level of immunocompetence. The role of the immune system is to discriminate the self from the nonself in order to eliminate pathogenic agents and spontaneous tumors. Any cell depletion, any immune disorder or any functional deficiency is capable of promoting the appearance of pathological manifestations characterized by the perturbation of the mechanisms of recognition of the self against the nonself, and a greater sensitivity towards microbial attacks and neoplastic processes.

The skin is the most important organ of the organism and is recognized as being one of the principal active components of the immune defense system. Three types of skin cells are involved in this system: the keratinocytes, the melanocytes and the Langerhans cells. These cells, which are encountered only in the skin, play a vital role in the immune response and in particular in antigen presentation.

Healthy skin is capable of defending itself against external attacks by virtue of the continuity and chemical nature thereof. Nevertheless, it is subjected to continuous attack by the environment, by chemical species and by radiations. The Langerhans cells in particular are the primary target of ultraviolet radiations.

These attacks are reflected in a suppressing effect on the immune defenses, resulting in a lowering in resistance to pathogenic agents and an increase in the incidence of some cancers.

To assist the skin to fulfil its immune function, species or substrates for stimulating the cutaneous immune system are of great interest.

It is known, moreover, that the immune system, and more particularly that of the skin, becomes weaker in the course of chronobiological aging.

This weakening also occurs during photo-induced aging.

An immuriostimulating effect can then restore the immune functions and more particularly those of the epidermis, by reinforcing the skin's natural defenses.

This invention therefore also features novel immunostimulants, more particularly for the immune system of the skin.

The present invention also features cosmetic or pharmaceutical compositions comprising at least one ribosomal fraction of at least one nonphotosynthetic filamentous bacterium.

The ribosomal fraction of at least one nonphotosynthetic filamentous bacterium displays marked ability to stimulate the immune system.

Thus, this invention more particularly features cosmetic or pharmaceutical compositions comprising, as the immunostimulating principle thereof, at least one ribosomal fraction of at least one nonphotosynthetic filamentous bacterium.

The ribosomal fraction is preferably utilized to stimulate the immune system of the skin. This stimulation of the immune system of the skin is particularly advantageous during chronobiological aging and/or photoaging.

The ribosomal fraction of the invention originates from bacteria selected from among nonphotosynthetic filamentous bacteria as defined in the classification of Bergey's *Manual of Systematic Bacteriology* (vol. 3, sections 22 and 23, 9th edition, 1989), among which are exemplary the bacteria belonging to the order of the Beggiatoales, and more particularly the bacteria belonging to the species Beggiatoa, Vitreoscilla, Flexithrix or Leucothrix.

The bacteria generally defined above, certain of which being specifically described, typically have an aquatic habitat and are located, especially in seawater or in thermal waters. Exemplary such bacteria include:

*Vitreoscilla filiformis* (ATCC 15551)

*Vitreoscilla beggiatoides* (ATCC 43181)

*Beggiatoa alba* (ATCC 33555)

*Flexithrix dorotheae* (ATCC 23163)

*Leucothrix mucor* (ATCC 25107)

*Sphaerotilus natans* (ATCC 13338)

A strain of *Vitreoscilla filiformis* is preferably employed according to the invention.

Any technique for preparation of a ribosomal fraction known to this art can be employed according to the invention.

The techniques described by Norris and Ribbons in *Methods in Microbiology*, 1973, (Academic Press) are particularly representative.

In the compositions according to the invention, the ribosomal fraction of at least one nonphotosynthetic filamentous bacterium advantageously constitutes from 0.0001% to 20% of the total weight of the composition and preferably from 0.01% to 10% of the total weight of the composition.

Depending on whether the fraction is employed in a composition which is to be ingested, injected or applied to the skin (to any region of the skin of the body), the hair, the nails or the mucosae (buccal, jugal, gingival, genital, anal or connective), this composition may be in any of the galenic forms normally employed.

For topical application to the skin, the composition may be formulated, especially, as an aqueous or oily solution, or as a dispersion of the lotion or serum type, or as emulsions of liquid or semiliquid consistency of the milk type, which are obtained by dispersing a fatty phase in an aqueous phase (O/W) or vice versa (W/O), or as suspensions or emulsions of soft consistency of the aqueous or anhydrous cream or gel type, or else as microcapsules or microparticles, or as vesicular dispersions of the ionic and/or nonionic type. These compositions are formulated via conventional techniques.

They may also be employed for the hair or the scalp, in the form of aqueous, alcoholic or hydroalcoholic solutions or in the form of creams, gels, emulsions, foams or else in the form of compositions for an aerosol also including a propellant under pressure.

In the case of injection, the composition may be in the form of an aqueous or oily lotion or in the form of a serum. In the case of the eyes, it may be in the form of drops and, for oral or ingestion administration, it may be in the form of capsules, granules, syrups or tablets.

The amounts of the various constituents of the compositions according to the invention are those conventionally employed in the particular fields under consideration.

For topical application to the skin, these compositions constitute, especially, cleaning, protecting and treating or care creams for the face, for the hands, for the feet, for the large anatomical creases or for the body (for example day creams, night creams, creams for removing makeup, foundation creams, sunscreen creams), fluid foundations, milks for removing makeup, body protection or care milks, sunscreen milks, lotions, gels or foams for skin care, such as cleaning lotions, sunscreen lotions, artificial tanning lotions, bath compositions, deodorizing compositions including a bactericidal agent, aftershave gels or lotions, depilatory creams, compositions against insect bites, pain-relief compositions and compositions for treating certain skin diseases, such as eczema, rosacea, psoriasis, lichens, severe pruritus and dermatitis.

The compositions may also be packaged in the form of an aerosol composition, also including a propellant under pressure.

The ribosomal fraction of at least one nonphotosynthetic filamentous bacterium employed according to the invention may also be incorporated into various compositions for hair care, and especially shampoos, hair setting lotions, treating lotions, styling creams or gels, dyeing compositions (especially oxidation dyes) optionally in the form of coloring shampoos, restructuring lotions for the hair, permanent-wave compositions (especially compositions for the first step of a permanent wave), lotions or gels for counteracting hair loss, antiparasite shampoos, and the like.

The compositions may also be for bucco-dental use, for example a toothpaste. In this case the compositions may contain the usual adjuvants and additives for compositions for buccal use and especially surface-active agents, thickening agents, moistening agents, polishing agents such as silica, various active ingredients such as fluorides, in particular sodium fluoride and optionally sweetening agents such as sodium saccharinate.

When the composition is an emulsion, the proportion of the fatty phase may range from 5% to 80% and preferably from 5% to 50% by weight relative to the total weight of the composition. The oils, waxes, emulsifiers and coemulsifiers employed in the composition in the form of an emulsion are selected from among those conventionally employed in the cosmetic field. The emulsifier and the coemulsifier are advantageously present in the composition in a proportion ranging from 0.3% to 30% by weight, and preferably from 0.5 to 20% by weight relative to the total weight of the composition. The emulsion may additionally contain lipid vesicles.

When the composition is a solution or an oily gel the fatty phase may constitute more than 90% of the total weight of the composition.

In known manner, any cosmetic composition may also contain adjuvants and additives which are usual in the cosmetic field, such as hydrophilic or lipophilic gelling agents, hydrophilic or lipophilic additives, preservatives, antioxidants, solvents, perfumes, fillers, filters, odor absorbers and colorants. The amounts of these various adjuvants and additives are those conventionally employed in the cosmetic field, and range for example from 0.01% to 10% of the total weight of the composition. Depending on their nature, these adjuvants and additives may be introduced in the fatty phase, in the aqueous phase and/or in the lipid spherules.

Exemplary oils or waxes that can be employed according to the invention include mineral oils (liquid petrolatum), vegetable oils (liquid fraction of karite butter, sunflower oil), animal oils (perhydrosqualene), synthetic oils (Purcellin oil), silicone oils or waxes (cyclomethicone) and fluorinated oils (perfluoropolyethers), beeswaxes and carnauba or paraffin waxes. Fatty alcohols and fatty acids (stearic acid) may be added to these oils.

Exemplary emulsifiers include, for example, glycerol stearate, polysorbate 60 and the mixture of PEG-6/PEG-32/glycol stearate, marketed by Gattefosse under the trademark Tefoseo® 63.

Exemplary solvents include the lower alcohols, especially ethanol and isopropanol, and propylene glycol.

And exemplary hydrophilic gelling agents include carboxyvinyl polymers (carbomer), acrylic copolymers such as acrylate/alkylacrylate copolymers, polyacrylamides, polysaccharides such as hydroxypropyl cellulose, natural gums and clays, and, exemplary lipophilic gelling agents, include the modified clays such as bentones, metal salts of fatty acids such as aluminum stearates and hydrophobic silica, ethyl cellulose and polyethylene.

The composition may contain other hydrophilic active species, such as proteins or protein hydrolysates, amino acids, polyols, urea, allantoin, sugars and sugar derivatives, water-soluble vitamins, plant extracts and hydroxy acids.

Lipophilic active agents which are exemplary are retinol (vitamin A) and derivatives thereof, tocopherol (vitamin E) and derivatives thereof, essential fatty acids, ceramides, essential oils, salicylic acid and derivatives thereof.

According to the invention, it is possible, inter alia, to employ a ribosomal fraction of at least one nonphotosynthetic filamentous bacterium in combination with other active agents intended, especially, for the prevention and/or treatment of skin disorders. Among these active agents, representative are, by way of example:

(1) agents modifying the differentiation and/or the proliferation and/or the pigmentation of the skin, such as retinoic acid and its isomers, retinol and its esters, vitamin D and derivatives thereof, oestrogens such as oestradiol, kojic acid or hydroquinone;

(2) antibacterial agents such as clindamycin phosphate, erythromycin or antibiotics of the tetracycline class;

(3) antiparasite agents, in particular metronidazole, crotamiton or the pyrethrinoids;

(4) antifungal agents, in particular the compounds belonging to the class of imidazoles, such as econazole, ketoconazole or miconazole or salts thereof, polyene compounds such as amphotericin B, compounds of the allylamine class such as terbinafine, or octopirox;

(5) antiviral agents such as acyclovir;

(6) steroidal anti-inflammatory agents such as hydrocortisone, betamethasone valerate or clobetasol propionate or nonsteroidal anti-inflammatory agents such as ibuprofen and salts thereof, diclofenac and salts thereof, acetylsalicylic acid, acetaminophene or glycyrrhetinic acid;

(7) anaesthetic agents such as lidocaine hydrochloride and its derivatives;

(8) anti-prurigenic agents such as thenaldine, trimeprazine or cyproheptadine;

(9) keratolytic agents such as alpha- and beta-hydroxycarboxylic or beta-ketocarboxylic acids, their salts, amides or esters and more particularly hydroxy acids such as glycolic acid, lactic acid, salicylic acid, citric acid and, in general, fruit acids and 5-n-octanoylsalicylic acid;

(10) agents for combatting free radicals, such as alpha-tocopherol or esters thereof, superoxide dismutases, certain metal-chelating agents or ascorbic acid and esters thereof;

(11) antiseborrhoeic agents such as progesterone;

(12) antidandruff agents such as octopirox or zinc pyrithione;

(13) antiacne agents such as retinoic acid or benzoyl peroxide.

Thus, in a preferred embodiment, this invention features compositions comprising at least one ribosomal fraction of at least one nonphotosynthetic filamentous bacterium and at least one agent selected from among antibacterial, antiparasite, antifungal, antiviral, anti-inflammatory, antiprurigenic, anaesthetic, keratolytic, anti-free radical, antiseborrhoeic, antidandruff, antiacne agents and/or agents modifying cutaneous differentiation and/or proliferation and/or pigmentation.

The present invention also features a regimen for cosmetic treatment with a view to stimulating the immune system and in particular the immune system of the skin, wherein a composition as described above is topically applied to the skin, to the hair and/or to the mucosae.

The cosmetic treatment of the invention is advantageously carried out by applying the hygienic or cosmetic compositions as defined above, via to the usual technique for application thereof. For example: application of creams, gels, serums, lotions, milks for removing makeup or sun protection compositions to the skin or to dry hair, application of a lotion for hair to wet hair, of shampoos, or else application of toothpaste to the gums.

In order to further illustrate the present invention and the advantages thereof, the following specific examples are given, it being understood that same are intended only as illustrative and in nowise limitative.

In said examples to follow, all parts and percentages are given by weight, unless otherwise indicated.

EXAMPLE 1

Preparation of a ribosomal fraction of *Vitreoscilla filiformis*

A *Vitreoscilla filiformis* culture was carried out according to the technique described in published French patent application No. 2,700,172, assigned to the assignee hereof.

100 ml of culture were then centrifuged for 10 minutes at 13,000 revolutions per minute at 4° C.

The supernatant was recovered. Ammonium sulfate at pH 7.5 was added in a proportion of 210 mg/ml.

Another centrifugation was carried out under conditions as indicated above.

The supernatant was dialyzed (spectra dialysis membranes, 1000 MWCO porosity (approximately 1,000 daltons)) against a Tris-HCl pH 7.6 buffer.

70 ml of ribosome-enriched medium were recovered.

EXAMPLE 2

Effect of a ribosomal fraction of *Vitreoscilla filiformis* on the growth and on the differentiation of 7-week Balb/c mouse splenocytes The ribosomal fraction from *Vitreoscilla filiformis* of Example 1 was tested at various concentrations in a model representing the activity of a substrate on the immune system: growth and differentiation of Balb/c mouse splenocytes aged 7 weeks.

The potential activity of the ribosomal fraction was evaluated:

(a) by measurement of the incorporation of thymidine into the deoxyribonucleic acid (proliferation index);

The negative control was represented by the effect of the culture medium on the splenocytes and the positive control by the effect of reference lipopolysaccharides (LPS) at 0.001% and 0.0001%. The LPSs employed were *Escherichia coli* LPSs marketed by Sigma.

Procedure for incorporation of tritiated thymidine

The mouse splenocytes were distributed into round-bottomed, 96-well NUNC culture dishes in a proportion of 250,000 cells per well in a final volume of 200 ml. The substrates to be tested were added to the wells in various concentrations. Cell proliferation was evaluated by incorporation of tritiated thymidine (1 µCi/well). 18 hours before the end of the culture 10 µl of tritiated thymidine containing 100 µCi/ml were added to each culture well. 18 hours later the cells were recovered on a filter with the aid of a Tomtec type cell harvester. The filter was then dried and covered with a scintillating liquid. The radioactivity deposited onto the filter was determined by counting in a β-type counter.

The proliferation was calculated using a stimulation index according to the following formula:

$$\frac{\text{Test radioactivity} - \text{control radioactivity (cells + medium)}}{\text{Control radioactivity}}$$

The results obtained are reported in Table I below: (value of the stimulation indices calculated according to the above formula)

TABLE I

| Ribosomal fraction | 24 h | 48 h | 72 h | 96 h |
|---|---|---|---|---|
| 5% | 1.02 | 4.08 | 3.10 | 1.97 |
| 2.5% | 1.84 | 8.18 | 8.03 | 2.87 |
| 1.25% | 1.64 | 4.80 | 2.03 | 0.89 |
| 0.63% | 1.61 | 4.56 | 3.81 | 1.33 |
| 0.31% | 1.63 | 3.97 | 4.66 | 4.16 |
| LPS | | | | |
| 0.001% | 1.50 | 5.47 | 13.64 | 16.48 |
| 0.0001% | 1.03 | 1.03 | 2.47 | 5.32 |

The ribosomal fraction increased the proliferation indices very significantly. The maximum effect was obtained at a concentration of 2.5% and after 48 hours of culture.

The effect was comparable with that obtained with the positive control.

(b) by measurement of the production of immunoglobulins after differentiation of the total splenocytes as B cells (B lymphocytes).

The negative control was represented by the effect of the culture medium on the splenocytes and the positive control by the effect of reference lipopolysaccharides (LPS) at 0.001% and 0.0001%. The LPSs employed were *Escherichia coli* LPSs marketed by Sigma.

Assay of the immunoglobulins

The cells were cultured under the same conditions as those described above. After 2 days of culture, the supernatants were removed and assayed for the presence of immunoglobulins (Ig).

This assay was carried out with the aid of a Pharmingen Kit, according to the supplier's procedure.

The immunoglobulins are proteins present in the blood which combine with antigens in order that the latter should be recognized and identified as a foreign body by the B lymphocytes.

The immunoglobulins are subdivided into various types and subtypes as a function of the structure of the constant part of their heavy chain. 5 classes (Ig M, G, A, D and E) are distinguished in the mouse. The immunoglobulin G is the most abundant immunoglobulin in body fluids, especially extravascular fluids, where it combats microorganisms and toxins. The G immunoglobulins can be classified into 4 subclasses (1, 2, 3 and 4).

Immunoglobulin A is the major immunoglobulin in the sero-mucosal secretions, in which it defends the external surfaces of the body.

Immunoglobulin M is a highly efficient agglutinating agent produced very early in the immune response. It constitutes the first line of defence against bacteraemias.

Only the Ig G1, G2a, G2b, G3, M and A were assayed in this test.

The results obtained are reported in Table II below:

TABLE II

| | IgG 1 | IgG 2a | IgG 2b | IgB 3 | IgM | IgA |
|---|---|---|---|---|---|---|
| Control | 1 | 1 | 1 | 1 | 1 | 1 |
| 0.001 LPS | 3.4 | 3.7 | 3.2 | 3.4 | 2.9 | 3.5 |
| 0.0001 LPS | 3 | 3.3 | 3.1 | 3.2 | 3 | 3 |
| 5% R.F. | 2.1 | 2.2 | 2.2 | 2.1 | 2.2 | 2.3 |
| 2.5% R.F. | 3.3 | 3.3 | 3 | 3.1 | 2.9 | 3.4 |
| 1.25% R.F. | 3.8 | 3.9 | 3.4 | 3.6 | 3.3 | 4 |

R.F. = ribosomal fraction.

The ribosomal fraction significantly increased the production of immunoglobulins of all classes and subclasses studied. The optimum active concentration was 1.25%.

These results were comparable with those obtained with the positive control.

EXAMPLE 3

Example of compositions according to the invention. These compositions were formulated via conventional techniques which are well known to this art.

| Cleaning cream: | |
|---|---|
| (a) Ribosomal fraction of Example 1 | 0.50 |
| (b) Cetyl alcohol | 2.00 |
| (c) Glycerol stearate | 2.00 |
| (d) Stearic acid | 2.00 |
| (e) Polyglyceryl-3-hydroxylauryl ether | 5.00 |
| (f) Codex mineral oil | 12.00 |
| (g) Carbomer | 0.35 |
| (h) Sodium hydroxide | 0.15 |
| (i) Perfume | q.s. |
| (j) Methylparaben | 0.20 |
| (k) Sterile demineralized water | q.s. 100.00 |
| Cleaning milk: | |
| (a) Ribosomal fraction of Example 1 | 0.50 |
| (b) Carbomer | 0.40 |
| (c) Sodium hydroxide | 0.10 |
| (d) Codex mineral oil | 5.00 |
| (e) Glycerol stearate | 1.00 |
| (f) Cetyl alcohol | 0.50 |
| (g) PEG 100 stearate | 0.80 |
| (h) Methylparaben | 0.20 |
| (i) Perfume | q.s. |
| (j) Sterile demineralized water | q.s. 100.00 |
| Care lotion: | |
| (a) Ribosomal fraction of Example 1 | 1.00 |
| (b) Glycerol | 2.00 |
| (c) Methylparaben | 0.15 |
| (d) Perfume | q.s. |
| (e) Sterile demineralized water | q.s. 100.00 |
| Care cream: | |
| (a) Ribosomal fraction of Example 1 | 2.00 |

-continued

| | |
|---|---|
| (b) Glycerol stearate | 1.00 |
| (c) PEG 100 stearate | 1.00 |
| (d) Stearic acid | 1.00 |
| (e) Cetyl alcohol | 2.00 |
| (f) Soya oil | 3.00 |
| (g) Palm oil | 2.00 |
| (h) Cyclomethicone | 2.00 |
| (i) Dimethicone | 1.00 |
| (j) Polyacrylamide | 0.20 |
| (k) Glycerol | 3.00 |
| (l) Methylparaben | 0.20 |
| (m) Perfume | q.s. |
| (n) Demineralized sterile water | q.s. 100.00 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A composition consisting essentially of a purified ribosomal fraction separated from a bacterium or a mixture of bacteria belonging to the order Beggiatoales.

2. The composition according to claim 1, wherein said purified ribosomal fraction is obtained from a bacterium belonging to the genus Beggiatoa, Vitreoscilla, Flexithrix or Leucothrix.

3. The composition according to claim 2, wherein said bacterium is a strain of *Vitreoscilla filiformis*.

4. A cosmetic or pharmaceutical composition of matter consisting essentially of a cosmetically or pharmaceutically effective amount of a purified ribosomal fraction separated from a bacterium or a mixture of bacteria belonging to the order Beggiatoales, and a pharmaceutically acceptable carrier.

5. The cosmetic or pharmaceutical composition as defined by claim 4, wherein said purified ribosomal fraction has immunostimulant activity.

6. The cosmetic or pharmaceutical composition as defined by claim 5, wherein said purified ribosomal fraction stimulates a skin immune response.

7. The cosmetic or pharmaceutical composition as defined by claim 4, wherein said purified ribosomal fraction constitutes from 0.01% to 10% of the total weight thereof.

8. A method for the treatment of a mammalian organism in need of such treatment, comprising topically applying to the skin, hair and/or mucosae of such organism, an effective amount of the cosmetic or pharmaceutical composition as defined by claim 4.

9. The cosmetic or pharmaceutical composition as defined by claim 4, wherein the composition is in the form of a lotion, milk, emulsion, gel, cream, solution, dispersion, suspension, microparticles, foam, aerosol, capsule, granule, syrup, tablet, shampoo or toothpaste.

10. A method for stimulating the immune system of a mammalian organism in need of such stimulation, comprising administering to such organism an effective amount of the cosmetic or pharmaceutical composition as defined by claim 4.

11. The cosmetic or pharmaceutical composition of claim 9, wherein said capsule is a microcapsule.

* * * * *